(12) United States Patent
Sidawi et al.

(10) Patent No.: US 10,675,373 B2
(45) Date of Patent: Jun. 9, 2020

(54) FRAGRANCE DISPENSER HAVING A DISPOSABLE PIEZOELECTRIC CARTRIDGE WITH A SNAP-IN BOTTLE CONTAINING AROMATIC LIQUID

(71) Applicants: Rami Sidawi, Milton (CA); Asad Rahman, Keswick (CA)

(72) Inventors: Rami Sidawi, Milton (CA); Asad Rahman, Keswick (CA)

(73) Assignee: Newmarket Concepts, LLC, Chicago, IL (US)

( * ) Notice: Subject to any disclaimer, the term of this patent is extended or adjusted under 35 U.S.C. 154(b) by 0 days.

(21) Appl. No.: 15/662,272

(22) Filed: Jul. 27, 2017

(65) Prior Publication Data

US 2018/0043048 A1     Feb. 15, 2018

Related U.S. Application Data

(60) Provisional application No. 62/367,241, filed on Jul. 27, 2016.

(51) Int. Cl.
*A61L 9/00* (2006.01)
*A61L 9/12* (2006.01)
(Continued)

(52) U.S. Cl.
CPC .......... *A61L 9/127* (2013.01); *B05B 17/0607* (2013.01); *B05B 17/0646* (2013.01);
(Continued)

(58) Field of Classification Search
CPC .... B01F 3/04; B01F 3/04007; B01F 3/04085;
B05B 17/0646; B05B 17/0684; B41J 2/1755; B41J 2/17523; B41J 2/17526; B41J 2/17553; B41J 2/14024; B41J 2/14072; B41J 2/14362; A61L 9/14; A61L 9/03; A61L 9/015
(Continued)

(56) References Cited

U.S. PATENT DOCUMENTS

| 5,223,182 A | * | 6/1993 | Steiner | A61L 9/122 |
| | | | | 261/26 |
| 5,305,541 A | * | 4/1994 | Simpson | A01M 31/008 |
| | | | | 43/1 |

(Continued)

FOREIGN PATENT DOCUMENTS

WO     2005097349 A1     10/2005

*Primary Examiner* — Viet Le
(74) *Attorney, Agent, or Firm* — McAndrews, Held & Malloy, Ltd.

(57) ABSTRACT

A fragrance dispenser unit has a piezoelectric discharge nozzle and a disposable snap-in air freshener containing aromatic liquid. The dispenser unit incorporates a battery power source and a piezoelectric driver circuit on a printed circuit board. The dispenser unit The cartridge includes a housing and an induction-sealed fragrance bottle that snaps into a socket at the bottom of the housing when the cartridge is to be activated. A membrane seal on the mouth of the bottle is pierced by a knife in the housing as the bottle is snapped into place. Liquid fragrance is directed to a microperforated vibratory plate in the piezoelectric nozzle by an airtight path that includes: first, a horizontal channel; second, a vertical wick; and, finally, a horizontal wick.

13 Claims, 6 Drawing Sheets

(51) Int. Cl.
*B05B 17/06* (2006.01)
*B05B 17/00* (2006.01)
*A61L 9/14* (2006.01)

(52) U.S. Cl.
CPC ............ *B05B 17/0684* (2013.01); *A61L 9/14* (2013.01); *A61L 2209/132* (2013.01); *A61L 2209/133* (2013.01)

(58) Field of Classification Search
USPC ........ 239/102.1, 102.2; 261/142, 94, 97, 99, 261/DIG. 65, DIG. 88, DIG. 89; 347/49, 347/50, 65, 85, 86
See application file for complete search history.

(56) References Cited

U.S. PATENT DOCUMENTS

| | | | | |
|---|---|---|---|---|
| 5,435,462 A * | 7/1995 | Fujii | B05C 17/015 | 222/144.5 |
| 5,529,055 A * | 6/1996 | Gueret | B05B 17/0646 | 128/200.16 |
| 5,657,926 A * | 8/1997 | Toda | B05B 17/0646 | 239/102.1 |
| 5,975,675 A * | 11/1999 | Kim | B41J 3/407 | 347/20 |
| 6,014,970 A * | 1/2000 | Ivri | A61M 15/0085 | 128/200.14 |
| 6,170,937 B1 * | 1/2001 | Childers | B41J 2/16538 | 347/85 |
| 6,196,219 B1 * | 3/2001 | Hess | A61M 15/0085 | 128/200.21 |
| 6,261,347 B1 * | 7/2001 | Moreland | C09D 11/38 | 106/31.02 |
| 6,293,474 B1 * | 9/2001 | Helf | A01M 1/205 | 239/102.1 |
| 6,296,196 B1 * | 10/2001 | Denen | A01M 1/205 | 239/102.1 |
| 6,322,200 B1 * | 11/2001 | Feinn | B41J 2/14024 | 347/50 |
| 6,323,912 B1 * | 11/2001 | McIntyre | H04N 1/2112 | 348/552 |
| 6,325,475 B1 | 12/2001 | Hayes et al. | | |
| 6,341,732 B1 * | 1/2002 | Martin | B05B 17/0646 | 128/200.16 |
| 6,357,671 B1 * | 3/2002 | Cewers | B05B 12/081 | 239/102.1 |
| 6,371,451 B1 * | 4/2002 | Choi | A45D 34/02 | 261/115 |
| 6,554,201 B2 | 4/2003 | Klimowicz et al. | | |
| 6,793,149 B2 * | 9/2004 | Schramm | A01M 1/205 | 239/102.1 |
| 6,802,460 B2 * | 10/2004 | Hess | A61L 2/18 | 239/102.1 |
| 6,808,684 B2 | 10/2004 | Boden et al. | | |
| 6,820,821 B2 * | 11/2004 | Linstedt | A47K 3/281 | 239/222.11 |
| 6,857,580 B2 * | 2/2005 | Walter | B05B 17/0607 | 239/102.1 |
| 6,968,124 B1 * | 11/2005 | Varanasi | A01M 1/2077 | 392/392 |
| 7,017,829 B2 * | 3/2006 | Martens, III | B05B 17/0646 | 239/326 |
| 7,090,257 B2 * | 8/2006 | Werth | A61M 39/00 | 285/243 |
| 7,152,758 B2 * | 12/2006 | Fazzio | A45D 34/02 | 222/145.1 |
| 7,281,811 B2 * | 10/2007 | Thuot Rann | A61L 9/037 | 219/220 |
| 7,367,661 B2 * | 5/2008 | Hess | B05B 17/0638 | 239/102.1 |
| 7,469,844 B2 * | 12/2008 | Conway | A61L 9/127 | 239/102.2 |
| 7,708,256 B2 * | 5/2010 | Pankhurst | A61L 9/02 | 261/104 |
| 8,006,918 B2 * | 8/2011 | Mahoney, III | H01L 41/042 | 239/102.1 |
| 8,020,573 B2 * | 9/2011 | Lamers | A61L 9/14 | 137/12 |
| 8,170,405 B2 * | 5/2012 | Harris | A01M 1/2033 | 392/386 |
| 8,251,500 B2 * | 8/2012 | Yamada | B41J 2/185 | 347/86 |
| 8,342,664 B2 * | 1/2013 | Wang | B41J 2/17513 | 347/7 |
| 8,348,177 B2 * | 1/2013 | Loverich | A01M 1/205 | 239/102.1 |
| 8,439,280 B2 * | 5/2013 | Marchetti | A61L 9/14 | 239/102.1 |
| 8,540,169 B2 * | 9/2013 | Kambayashi | A01M 1/205 | 239/102.1 |
| 8,584,967 B2 * | 11/2013 | Feriani | B05B 17/0638 | 239/102.1 |
| 8,625,977 B2 * | 1/2014 | Cheung | A61L 9/037 | 392/386 |
| 8,708,470 B1 * | 4/2014 | Blowfield | B41J 2/17523 | 347/86 |
| 8,727,234 B2 | 5/2014 | Haran | | |
| 8,851,644 B2 * | 10/2014 | Shirono | B41J 2/17506 | 347/84 |
| 8,870,090 B2 | 10/2014 | Feriani et al. | | |
| 8,925,833 B2 * | 1/2015 | Ki | A45D 34/04 | 239/102.1 |
| 9,067,425 B2 * | 6/2015 | Blowfield | B41J 2/17526 | |
| 9,095,671 B2 * | 8/2015 | Feriani | A61M 11/005 | |
| 9,168,756 B2 * | 10/2015 | Harada | B41J 2/1721 | |
| 9,211,980 B1 * | 12/2015 | Gruenbacher | A61L 9/14 | |
| 9,278,365 B2 * | 3/2016 | Banco | B05B 7/2491 | |
| 9,333,523 B2 * | 5/2016 | Lowy | B05B 17/0646 | |
| 9,474,824 B2 * | 10/2016 | Conroy | G06Q 10/08 | |
| 2002/0114744 A1 * | 8/2002 | Chiao | A61L 9/014 | 422/124 |
| 2002/0144678 A1 * | 10/2002 | Warby | A61M 15/009 | 128/200.23 |
| 2002/0192255 A1 * | 12/2002 | Schiavo | A01M 1/2077 | 424/405 |
| 2003/0146292 A1 * | 8/2003 | Schramm | A01M 1/205 | 239/4 |
| 2003/0206834 A1 * | 11/2003 | Chiao | A61L 9/014 | 422/124 |
| 2003/0218077 A1 * | 11/2003 | Boticki | B05B 17/0646 | 239/102.1 |
| 2004/0032468 A1 * | 2/2004 | Killmeier | B41J 2/1753 | 347/85 |
| 2004/0144853 A1 * | 7/2004 | Helf | A47F 7/286 | 239/4 |
| 2004/0195351 A1 * | 10/2004 | Leonard | A01M 1/2033 | 239/102.1 |
| 2004/0235430 A1 * | 11/2004 | Ma | A61L 9/03 | 455/90.1 |
| 2005/0109859 A1 * | 5/2005 | Gau | B05B 17/0638 | 239/102.1 |
| 2005/0211797 A1 * | 9/2005 | Abergel | A61L 9/12 | 239/333 |
| 2006/0011737 A1 * | 1/2006 | Amenos | A01M 1/2033 | 239/102.1 |
| 2006/0065755 A1 * | 3/2006 | Sugita | A61M 15/0065 | 239/1 |
| 2006/0243820 A1 * | 11/2006 | Ng | B05B 17/0646 | 239/102.1 |
| 2006/0289673 A1 * | 12/2006 | Wang | B05B 17/0646 | 239/102.1 |
| 2007/0020033 A1 * | 1/2007 | Walsh | B43K 5/005 | 401/195 |
| 2007/0138326 A1 * | 6/2007 | Hu | A01M 1/2038 | 239/690 |
| 2008/0164339 A1 * | 7/2008 | Duru | B05B 17/0646 | 239/102.2 |

(56) References Cited

U.S. PATENT DOCUMENTS

| | | | | |
|---|---|---|---|---|
| 2009/0301472 | A1* | 12/2009 | Kim | A61M 15/0085 |
| | | | | 128/200.16 |
| 2010/0154790 | A1* | 6/2010 | Merassi | B05B 1/14 |
| | | | | 128/200.18 |
| 2010/0206306 | A1* | 8/2010 | Feriani | A61M 11/00 |
| | | | | 128/203.12 |
| 2011/0011948 | A1* | 1/2011 | Huang | B05B 17/0607 |
| | | | | 239/44 |
| 2011/0290241 | A1* | 12/2011 | Maeda | A61M 11/005 |
| | | | | 128/200.14 |
| 2012/0018529 | A1* | 1/2012 | Gammon | A61L 9/03 |
| | | | | 239/6 |
| 2013/0334336 | A1* | 12/2013 | Haran | A61L 9/14 |
| | | | | 239/4 |
| 2014/0063113 | A1* | 3/2014 | Irving | B41J 2/17513 |
| | | | | 347/20 |
| 2014/0078229 | A1* | 3/2014 | Jackson | A61L 9/14 |
| | | | | 347/95 |
| 2015/0367013 | A1* | 12/2015 | Gruenbacher | A45D 34/00 |
| | | | | 239/13 |
| 2015/0367014 | A1* | 12/2015 | Gruenbacher | A61L 9/03 |
| | | | | 392/387 |
| 2015/0367016 | A1* | 12/2015 | Gruenbacher | A45D 34/00 |
| | | | | 96/222 |
| 2015/0367356 | A1* | 12/2015 | Gruenbacher | B05B 1/24 |
| | | | | 239/135 |
| 2015/0368001 | A1* | 12/2015 | Gruenbacher | A61L 9/14 |
| | | | | 222/52 |
| 2016/0228902 | A1* | 8/2016 | Crichton | A61M 35/00 |
| 2017/0211265 | A1* | 7/2017 | Pasquini | E03D 9/005 |
| 2017/0274405 | A1* | 9/2017 | Lucas | B05B 17/0646 |

\* cited by examiner

FRAGRANCE DISPENSER HAVING A DISPOSABLE PIEZOELECTRIC CARTRIDGE WITH A SNAP-IN BOTTLE CONTAINING AROMATIC LIQUID

RELATED APPLICATIONS

This application claims priority of a provisional patent application No. 62/367,241, titled DISPOSABLE CARTRIDGE HAVING A PIEZOELECTRIC DISCHARGE NOZZLE AND A SNAP-IN BOTTLE CONTAINING AROMATIC LIQUID, which was filed on Jul. 27, 2016.

FIELD OF THE INVENTION

This invention relates, generally, to fragrance dispensers and, more particularly, to battery-powered, wall-mounted fragrance dispensers having a replaceable refill cartridge.

BACKGROUND OF THE INVENTION

The annual market for air freshener products in the U.S. is over $3 billion. Plug-in type air freshener products account for a third of that market. Over the past decade, battery-operated, metered aerosol fragrance dispensers have become popular in commercial settings such as public and office restrooms. As these devices are typically somewhat complex, in that they incorporate a DC electric motor, a gear drive operated by the motor which actuates the spray valve, an aerosol fragrance canister, and a programmable timer for adjusting the time interval between sprays, average retail prices of around $50 were too costly to generate widespread demand for home use. However, prices have dropped dramatically. For example, Wal-Mart now sells a programmable Air Wick® dispenser with one aerosol fragrance canister for less than $10. As the cost of a replacement fragrance canister is nearly $4, it appears that American Home Products Corporation may be selling the Air Wick® fragrance dispenser at less than cost, a marketing strategy learned from Gillette's sale of razor blades and Hewlett-Packard's sale of ink cartridges.

One problem associated with the motor-operated fragrance dispensers is that the moving mechanical parts are the components most likely to fail over time. A simpler, more durable solution employs a micro-perforated plate secured to a piezoelectric vibrator that is energized by an AC voltage. Such devices have been used as humidifiers and as aerosol fragrance dispensers. U.S. Pat. No. 5,297,734 to Kohji Toda discloses such an ultrasonic vibrating device. The micro-perforations are conical and larger in diameter on the supply side, and the piezoelectric vibrator operates at a frequency of about 100 kHz.

U.S. Pat. No. 5,657,926, also to Kohji Toda, discloses an ultrasonic atomizing device that employs electrical feedback from the piezoelectric vibrator to generate a resonant frequency of greater amplitude to vibrate the micro-perforated plate.

U.S. Pat. No. 6,293,474 to Thomas A. Helf, et al. discloses a wick-based delivery system to provide liquid to a microperforated plate that is vibrated by a piezoelectric device.

U.S. Pat. No. 6,341,732 to Frederick H. Martin, et al. discloses a method and apparatus for maintaining control of liquid flow in a vibratory atomizing device. As with the '474 Patent to Helf, et al., liquid if provided to a vibrating orifice plate by a wick. However, liquid that is not expelled by the vibrating plate drains back through the plate and absorbed by the wick, which then provides it again to the vibrating plate.

SUMMARY OF THE INVENTION

The present invention provides a disposable air freshener cartridge having a piezoelectric discharge nozzle that installs within a wall-mounted dispenser unit, which incorporates a battery power source and a printed circuit board that provides a piezoelectric driver circuit. When installed in a dispenser unit, electrical contacts on the cartridge make physical contact with electrical contacts on the dispenser unit, thereby enabling the piezoelectric nozzle of the cartridge to be powered by the battery power source. The cartridge includes a housing having a base and a piezoelectric nozzle, and a bottle, containing liquid fragrance, that plugs into the base when the cartridge is to be used. The bottle has a mouth that is designed to snap into a socket in the base when the bottle is pressed into the body. The mouth of the bottle is equipped with a chamfered hook ring, and the socket is equipped with flexible chamfered hooks that engage and lock over the chamfered hook ring when the bottle is pressed into the socket of the base. The mouth of the bottle is induction sealed with a foil and polymeric membrane, and the socket incorporates a semi-cylindrical central projection that incorporates an upwardly-angled parabolic knife that punctures the membrane when the mouth is snapped into the socket. Because of the difficulty involved in preventing seepage and evaporation of the liquid fragrance before it is used, the bottle is installed within the cartridge, but the mouth of the bottle has not been seated within the socket. When the cartridge is ready for use, the bottle is pushed down so that the mouth of the bottle snaps into the socket, thereby rupturing the membrane seal on the mouth of the bottle and allowing the aromatic liquid to travel to the piezoelectric nozzle.

The base of the cartridge housing incorporates a longitudinal channel in the base that leads to a vertically-oriented wick that is installed within a vertical channel near the front of the cartridge. Opposite ends of a horizontal wick, installed within a horizontal cylindrical cavity, are in contact with the vertically-oriented wick and a micro-perforated vibratory plate that is embedded in a donut-shaped piezoelectric vibrator. Both the vibratory plate and the piezoelectric vibrator are installed within the discharge nozzle. The liquid fragrance path between the vibratory plate and the socket is airtight. When the aromatic liquid has been expended, the cartridge is extracted from the dispenser unit and replaced with a new one. Thus, cartridge replacement involves replacement of not only the aromatic liquid containing bottle, but the piezoelectric nozzle and wick system as well.

PREFERRED EMBODIMENT OF THE INVENTION

The various embodiments of the invention will now be described in detail with reference to the attached drawing figures. It is to be understood that the drawings are not necessarily drawn to scale and that they are intended to be merely illustrative.

Figure 1:
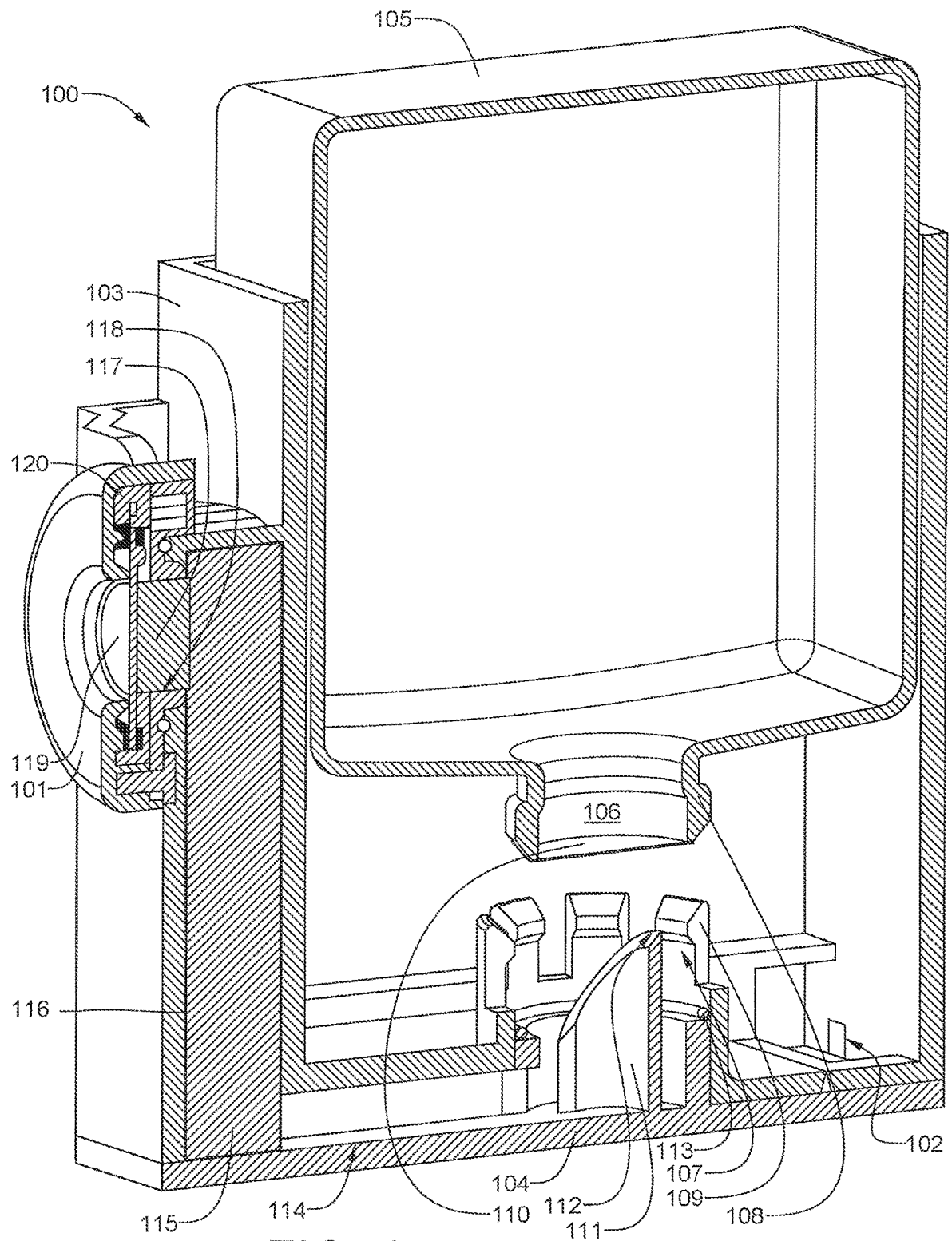
FIG. 1 is a cross-sectional isometric view of the piezoelectric cartridge, with the fragrance bottle positioned above the truncated cylindrical knife, taken through a vertical plane through the middle of the cartridge and the bottle.

Referring now to FIG. 1, the present invention provides a disposable air freshener cartridge 100 having a piezoelectric discharge nozzle 101 that installs within a wall-mounted dispenser unit (not shown in this view), which incorporates a battery power source and a printed circuit board that provides a piezoelectric driver circuit. When installed in the dispenser unit, electrical contacts on the cartridge make physical contact with electrical contacts on the dispenser unit, thereby enabling the piezoelectric nozzle 101 of the cartridge 100 to be powered by the driver circuit. It is contemplated that electrical wiring between the piezoelectric discharge nozzle 101 and the dispenser unit will be made through the rectangular aperture 102. The cartridge includes a body 103 having a base 104 and a piezoelectric discharge nozzle 101, and a bottle 105, containing liquid fragrance (not shown), that plugs into the base 104 when the cartridge is to be used. The bottle 105 has a mouth 106 that is designed to snap into a socket 107 in the base 104 when the bottle 105 is pressed into the body 103. The bottle mouth 106 is equipped with a chamfered securing ring 108, and the socket 107 is equipped with a plurality of flexible chamfered hooks 109 that engage and lock over the chamfered securing ring 108 when the bottle mouth 106 is pressed into the socket 107 of the base 104. The bottle mouth 106 is induction sealed with a foil and polymeric membrane 110, and the socket 107 incorporates a truncated semi-cylindrical knife 111 in the center thereof that forms an upwardly-angled sharpened parabolic edge that pierces the membrane 110 when the bottle 105 is snapped into the socket 107. The central projection 111 is in the shape of a truncated semi-cylindrical knife 111 that incorporates an upwardly-angled parabolic knife edge 112 that punctures the membrane 110 when the mouth 106 is snapped into the socket 107. Because of the difficulty involved in preventing seepage and evaporation of the liquid fragrance before it is used, the bottle 105 is shipped within the body 103 as shown, and kept separate until they are put into use. A rubber O-ring 113 that is installed within the socket 107 makes an airtight seal between the bottle mouth 106 and the socket 107.

Still referring to FIG. 1, the base 104 of the body 103 incorporates a longitudinal channel 114 in the base 104 that leads to a vertically-oriented wick 115 that is installed within a vertical channel 116 near the front of the body 103. Opposite ends of a horizontal wick 117, installed within a horizontal cylindrical cavity 118, are in contact with both the vertically-oriented wick 115 and a micro-perforated vibratory plate 119 that is embedded in a donut-shaped piezoelectric vibrator 120. Together, the vibratory plate 119 and the piezoelectric vibrator 120 make up the piezoelectric discharge nozzle 101. The liquid fragrance path between the vibratory plate 119 and the socket 107 is airtight. It should be understood that the cross-sectional view of FIG. 1 is taken through a vertical plane passing through the middle of the body 103 and bottle 105. The missing half of the bottle 105 is the mirror image of the half that is visible.

Figure 2:
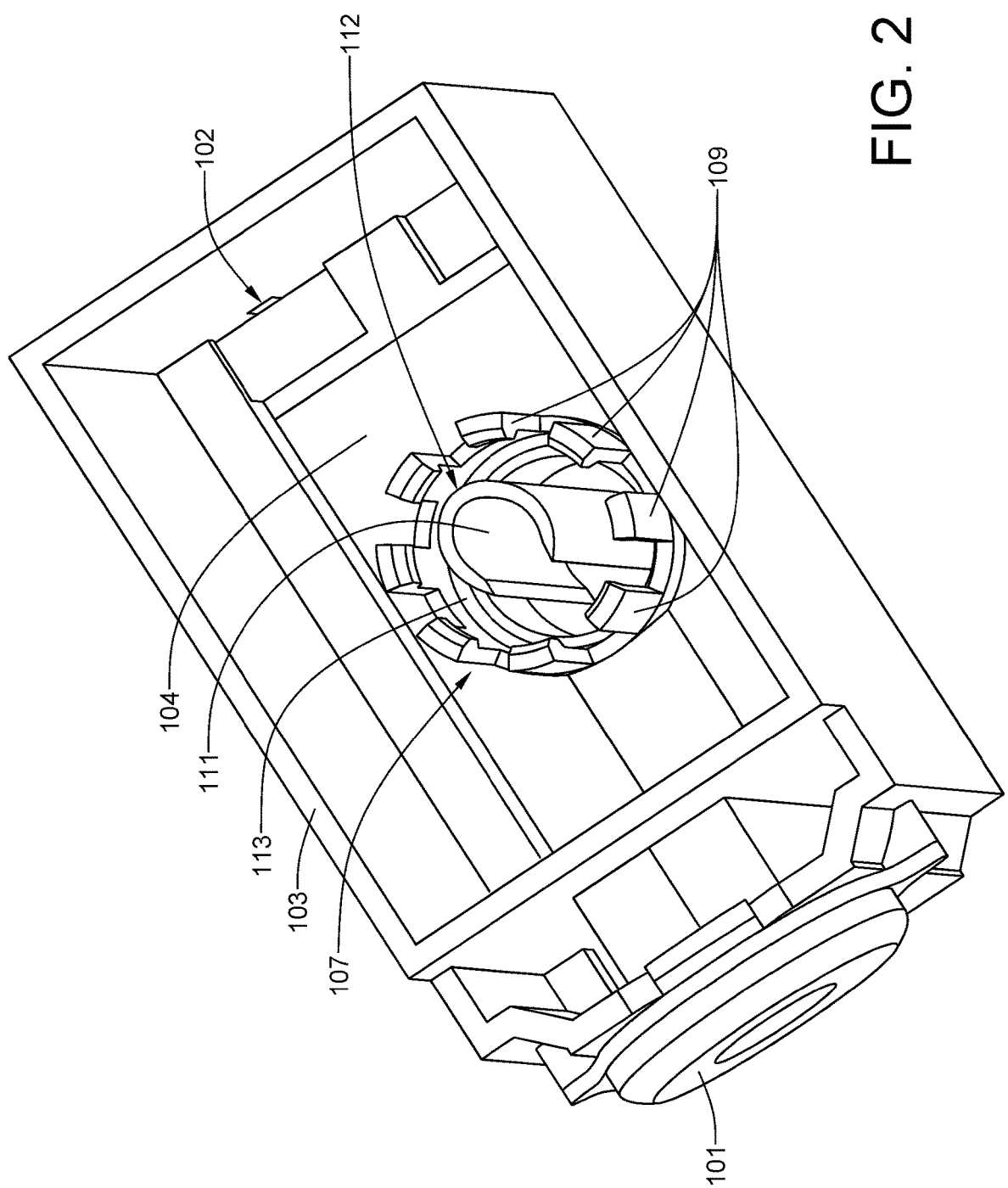
FIG. 2 is an isometric view of the cartridge with the fragrance bottle removed.

Referring now to FIG. 2, the disposable air freshener cartridge 100 is seen with the bottle 105 removed therefrom. The details of the socket 107 are visible in this view. The discharge nozzle 101, the body 103, the base 104, the flexible chamfered hooks 109, the truncated semi-cylindrical knife 111, and the upwardly-angled parabolic knife edge 112 are also clearly visible in this view.

Figure 3:
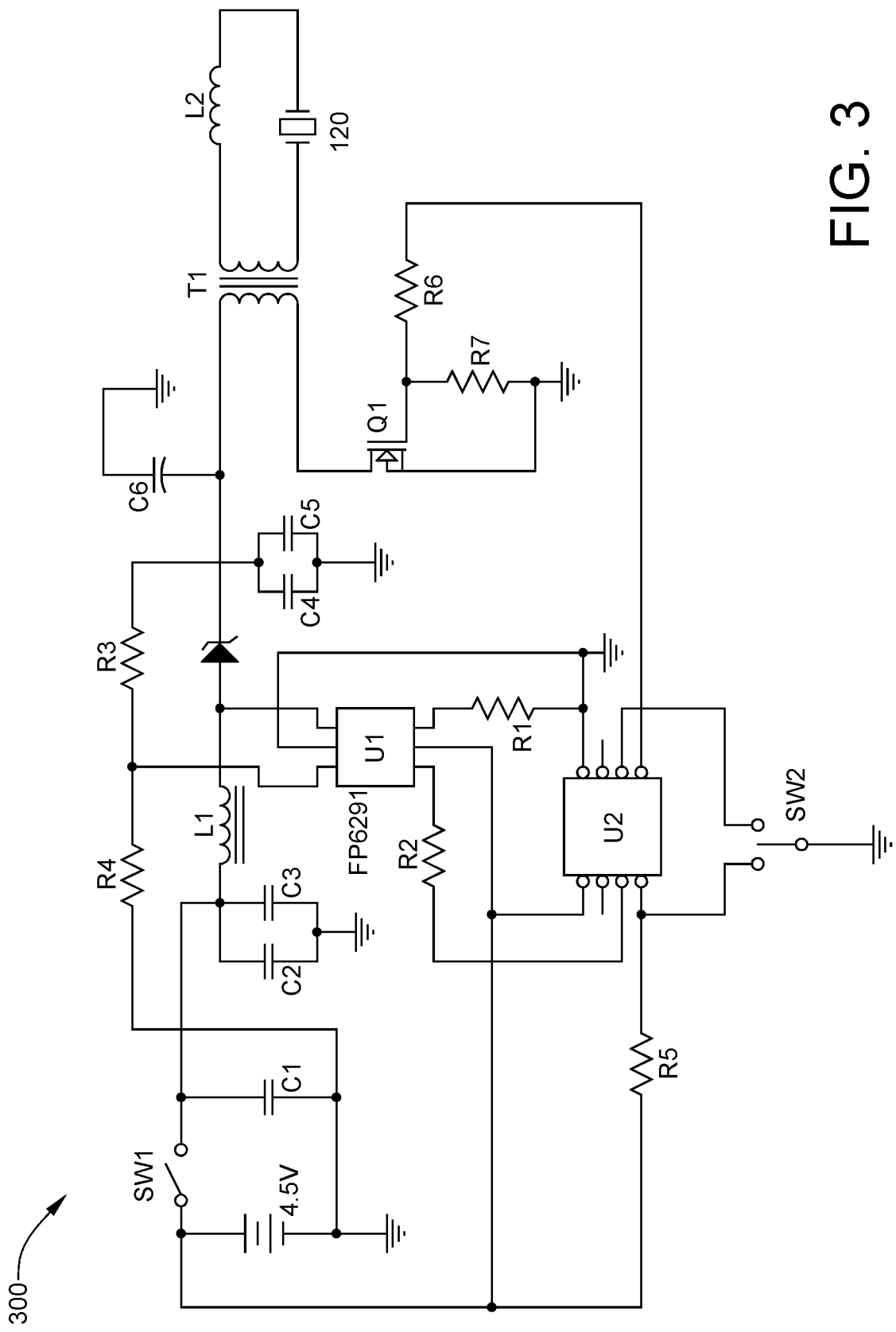
FIG. 3 is a driver circuit for the piezoelectric discharge nozzle.

Referring now to FIG. 3, the piezoelectric driver circuit 300 includes a 4.5-volt DC power source than can be provided by three series-coupled 1.5-volt cells, or by rectified AC power taken from a wall outlet. The primary function of the piezoelectric driver circuit 300 is to provide a pulse train that drives the piezoelectric crystal vibrator 120 that vibrates the vibratory plate 119. The main components of the circuit 300 are a a FP6291 current mode boost DC-DC converter U1 that provides regulated power that is sent in pulses through a transformer T1 in order to generate current levels required to excite the piezoelectric vibrator 120. The pulses are accurately sequenced and timed by a 555 digital timer U2, which controls the gate of transistor Q1. Current flows through the primary winding of transformer T1 when current flows through transistor Q1. When a pulse from the secondary winding of transformer T1 reaches the piezoelectric vibrator 120, a mist of atomized aromatic liquid droplets is expelled from the piezoelectric discharge nozzle 101. The piezoelectric driver circuit 300 also includes resistors R1, R2, R3, R4, R5, R6, and R7; capacitors C1, C2, C3, C3, C4, C5 and C6; inductances L1 and L2; and switches S1 and S2.

Figure 4:
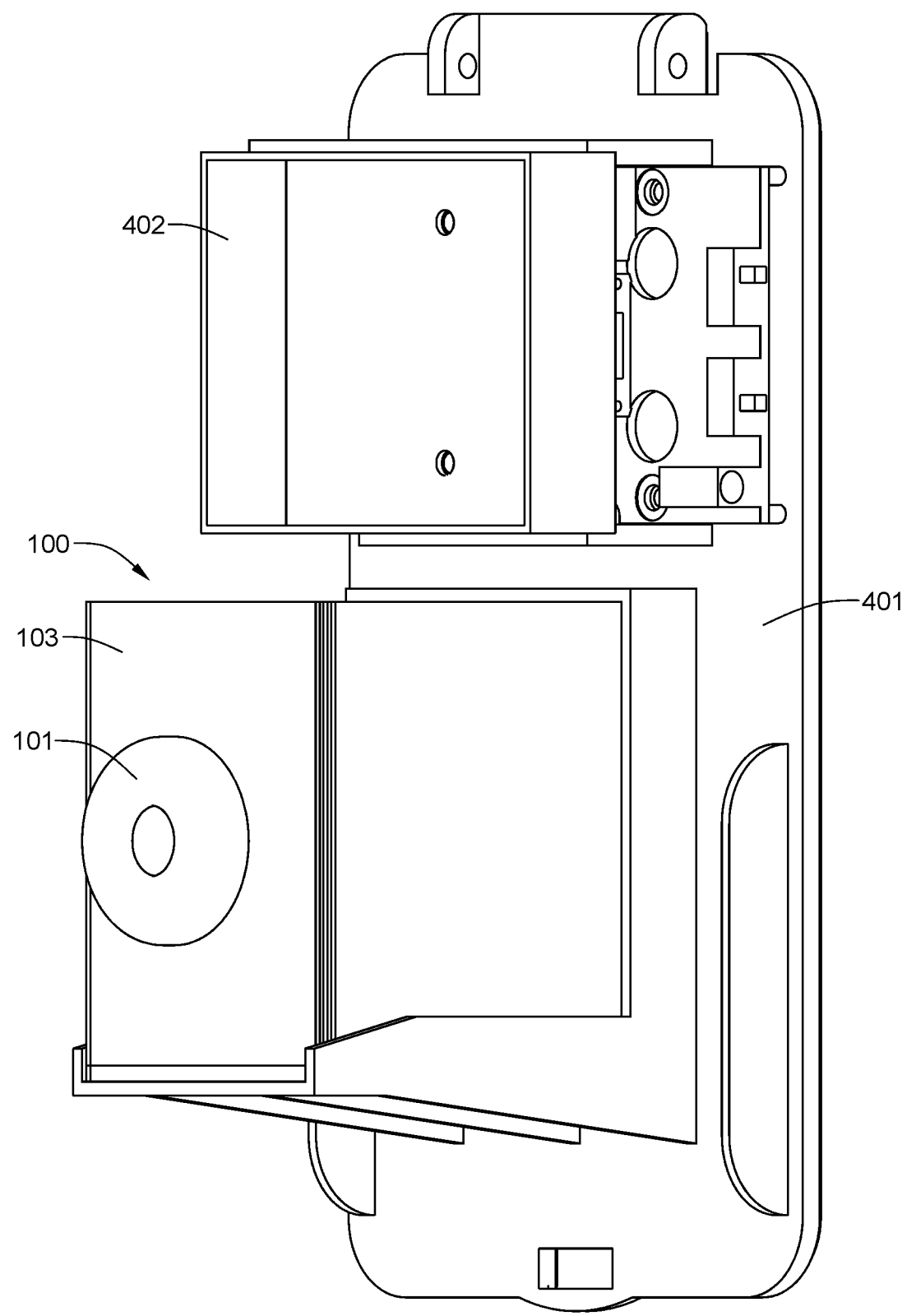
FIG. 4 is an isometric view of the housing backing plate with the piezoelectric cartridge installed thereon.
Figure 5:
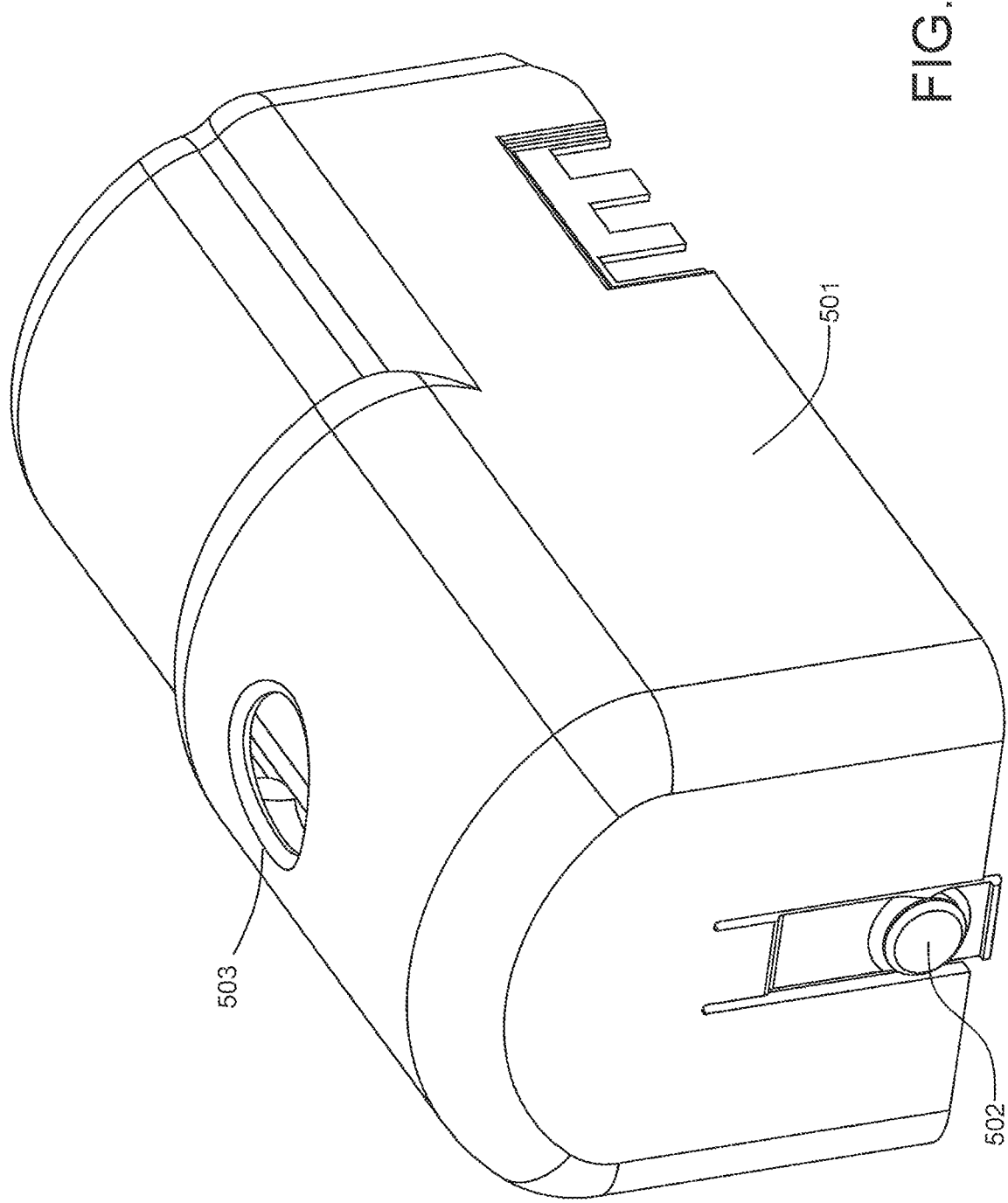
FIG. 5 is an isometric view of the top-hinged housing front cover.

Referring now to FIG. 4, the fragrance dispenser has a housing that includes a backing plate 401 and a top-hinged front cover (see FIG. 5). It will be noted that the piezoelectric air freshener cartridge 100 is installed on the backing plate 401. Above the cartridge is a battery compartment 402.

Referring now to FIG. 5, the top-hinged front cover 501 is shown in this figure. A spring-loaded release button 502 at the bottom rear of the front cover 501 can be depressed in order to release the front cover 501 from the backing plate 401 and raise the front cover 501 for access to the cartridge 100 and the battery compartment. The front of the front cover has an aperture 503 through which atomized aromatic liquid is released into the air. The aperture 503 is about centered in the front of the lower half of the cover.

Figure 6:
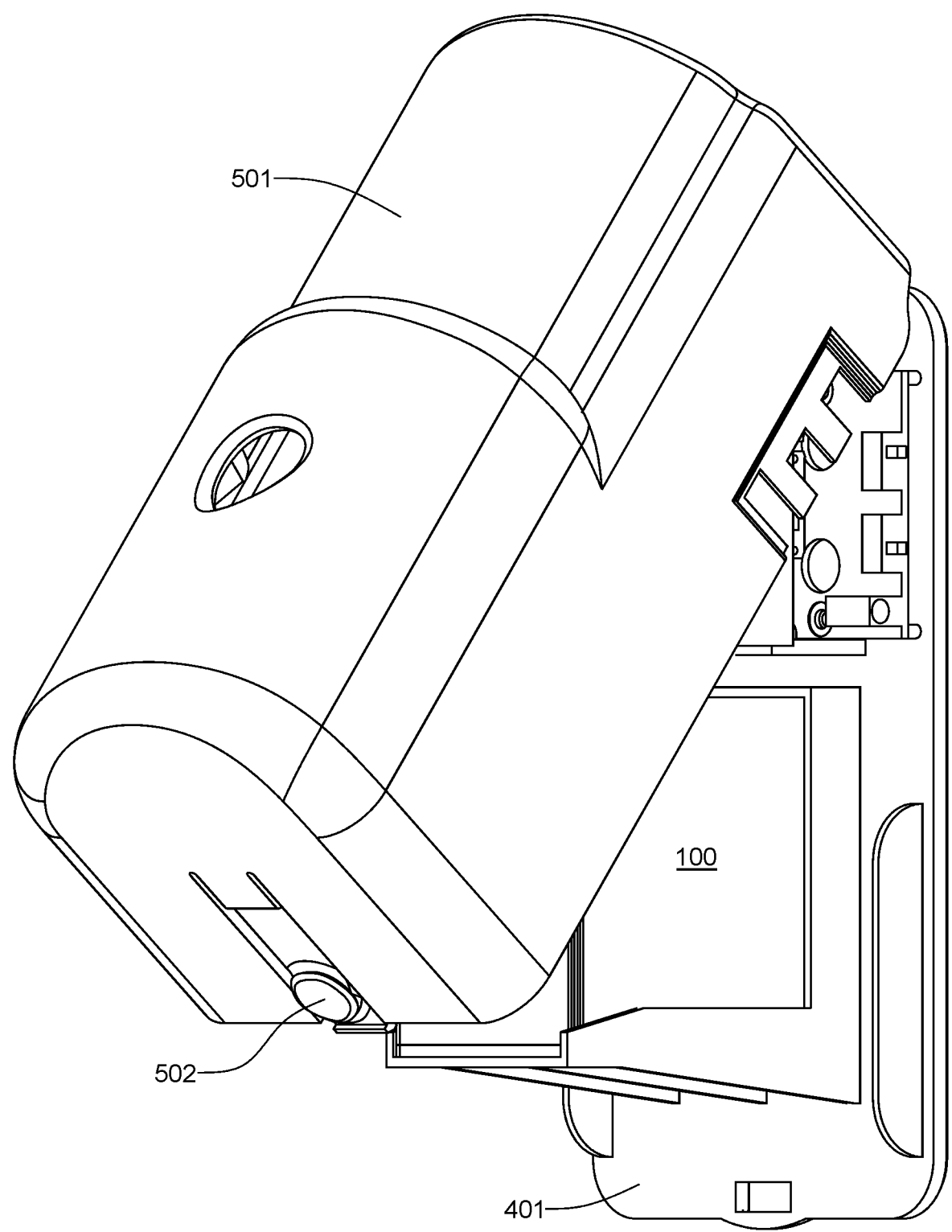
FIG. 6 is an isometric view of the complete housing, with the front cover hingedly attached to the backing plate.

Referring now to FIG. 6, the front cover 501 has been hingedly attached to the backing plate 401. The piezoelectric air freshener cartridge 100 can be partially seen in this view.

Although the fragrance dispenser is presently intended to mount on a wall, it can also be used as a free-standing device that sits on either a table or a shelf. As heretofore explained, it can be either battery powered or powered by a switching AC-DC power supply that plugs into a standard 120-240 v AC outlet.

Although only a single embodiment of the fragrance dispenser and piezoelectric air freshener cartridge 100 has been heretofore described, it will be obvious to those having ordinary skill in the art that changes and modifications may be made thereto without departing from the scope and the spirit of the invention as hereinafter claimed.

What is claimed is:

1. A fragrance dispensing system, comprising:
   a dispenser unit including a housing having a power source and a printed circuit board containing a piezoelectric driver circuit powered by said power source; and
   a piezoelectric cartridge installable within said housing and including:

a cartridge body;

a piezoelectric discharge nozzle supported by said cartridge body and having a micro-perforated vibratory plate, said discharge nozzle powered by said driver circuit of said dispenser unit when said piezoelectric cartridge is installed within said housing of said dispenser unit;

a fragrance bottle supported by said cartridge body, said cartridge body further having a liquid fragrance path from the bottle to the piezoelectric nozzle, said path including a channel with a wick, said wick in contact with the vibratory plate of the piezoelectric discharge nozzle, said piezoelectric cartridge further including a horizontal channel in fluid communication with the bottle and leading to a vertical portion of the wick, the wick further having a horizontal portion in contact with the vibratory plate.

2. The fragrance dispensing system of claim 1, wherein said housing of said dispenser unit further includes a cover with a discharge aperture that is aligned with the vibratory plate when the piezoelectric cartridge is installed so that atomized aromatic liquid from the piezoelectric discharge nozzle is released through the discharge aperture.

3. The fragrance dispensing system of claim 1, wherein said piezoelectric cartridge further includes a knife, and said fragrance bottle has a mouth that is hermetically sealed with a membrane, the knife positioned in the piezoelectric cartridge to pierce said membrane when the bottle is installed in the piezoelectric cartridge, thereby releasing the aromatic liquid into the liquid fragrance path.

4. The fragrance dispensing system of claim 1, wherein said power source is a battery power source.

5. The fragrance dispensing system of claim 1, wherein said piezoelectric driver circuit periodically sends a power pulse to the piezoelectric nozzle, which releases a controlled amount of aromatic liquid into the air with each pulse.

6. The fragrance dispensing system of claim 1, said piezoelectric cartridge further comprising a socket supported by said body, said bottle connectable to said socket to enable aromatic liquid to flow from the bottle to the piezoelectric nozzle via the liquid fragrance path.

7. The fragrance dispensing system of claim 6, said piezoelectric cartridge further comprising a knife positioned within the socket so that a membrane seal of the bottle is pierced by the knife when the bottle is installed in the piezoelectric cartridge.

8. The fragrance dispensing system of claim 1, wherein the channel of the piezoelectric cartridge with the wick is an airtight channel.

9. A piezoelectric fragrance cartridge for a fragrance dispenser unit, the fragrance dispenser unit including a housing with a power source and a piezoelectric driver circuit powered by the power source, the piezoelectric fragrance cartridge comprising:

a cartridge body;

a piezoelectric discharge nozzle supported by the body and including a micro-perforated vibratory plate;

a fragrance bottle supported by the body;

a liquid fragrance path from the bottle to the piezoelectric nozzle, said liquid fragrance path including a channel with a wick, said wick in contact with the vibratory plate of the piezoelectric discharge nozzle;

electrical contacts, wherein the piezoelectric fragrance cartridge is installable in the housing of the fragrance dispenser unit so that the electrical contacts of the piezoelectric fragrance cartridge engage with corresponding electrical contacts of the fragrance dispenser unit thereby enabling the piezoelectric nozzle of the piezoelectric cartridge to be powered by the piezoelectric driver circuit of the fragrance dispenser unit and release a mist of atomized aromatic liquid droplets from the piezoelectric discharge nozzle; and a horizontal channel in fluid communication with the bottle and leading to a vertical portion of the wick, the wick further having a horizontal portion in contact with the vibratory plate.

10. The piezoelectric fragrance cartridge of claim 9, further comprising:

a knife supported by the cartridge body; and a membrane positioned over an opening in the bottle to hermetically seal the opening, wherein the knife is positioned to pierce the membrane when the bottle is installed in the piezoelectric cartridge so that aromatic liquid from the bottle is released into the liquid fragrance path.

11. The piezoelectric fragrance cartridge of claim 9, further comprising:

a socket supported by said cartridge body, the bottle connectable to the socket to enable aromatic liquid to flow from the bottle to the piezoelectric nozzle via the liquid fragrance path.

12. The piezoelectric fragrance cartridge of claim 9, wherein the bottle is a snap-in bottle with a mouth configured to snap into the socket.

13. The piezoelectric fragrance cartridge of claim 9, wherein the channel with the wick is an airtight channel.

* * * * *